United States Patent
Humphrey (12)

(10) Patent No.: US 6,599,276 B1
(45) Date of Patent: Jul. 29, 2003

(54) DETECTABLE STAINLESS STEEL NEEDLES FOR MEAT PACKING

(75) Inventor: Grant S. Humphrey, Winnipeg (CA)

(73) Assignee: Process Detectable Needles, Inc., Winnipeg (CA)

( * ) Notice: Subject to any disclaimer, the term of this patent is extended or adjusted under 35 U.S.C. 154(b) by 0 days.

(21) Appl. No.: 09/501,518

(22) Filed: Feb. 9, 2000

(51) Int. Cl.[7] .................................................. A61M 5/00
(52) U.S. Cl. ........................ 604/272; 604/239; 604/264
(58) Field of Search ................................. 604/239, 264, 604/272

(56) References Cited

U.S. PATENT DOCUMENTS

| | | | |
|---|---|---|---|
| 4,409,046 A | | 10/1983 | Holzwarth et al. |
| 4,968,362 A | * | 11/1990 | Prasad .......................... 148/286 |
| 5,162,037 A | * | 11/1992 | Whitson-Fischman ........ 600/12 |
| 5,306,251 A | * | 4/1994 | Alexander .................... 604/130 |
| 5,433,711 A | * | 7/1995 | Balaban et al. ............... 604/192 |
| 5,651,843 A | * | 7/1997 | Bendel et al. ................ 148/327 |
| 5,814,166 A | | 9/1998 | Ackerman et al. |
| 5,894,015 A | * | 4/1999 | Rechtin ........................ 422/301 |
| 6,315,113 B1 | * | 11/2001 | Britton et al. ............... 206/210 |

FOREIGN PATENT DOCUMENTS

| | | |
|---|---|---|
| EP | 0030353 | 6/1981 |
| GB | 1217561 | 12/1970 |

OTHER PUBLICATIONS

H.K. Worner, An Investigation of Properties of Some Hypodermic Needles used in Dentistry, Australian Journal of Dentistry, vol. 44, No. 6, Jun. 1940 pp. 205–214.
ISO 9626 Jun. 01, 2000.
ASTM A 908–91 (Reapproved 1998) 1998.
S.J. Hott & P. Sunberg, Breakage & Deformation Characteristics of Hypodermic Devices Under Static & Dynamic Loading, 1999, AJVR, Go, No. 3, 292–298.
Donkersgoed, A Broken Needle in my Steak, Cattleman, 2000 p28.

* cited by examiner

*Primary Examiner*—J. Casimer Jacyna
(74) *Attorney, Agent, or Firm*—Ogilvy Renault; Paul S. Sharpe

(57) ABSTRACT

Magnetic stainless steel needles are detectable in processed meat. The previous non magnetic versions, made of 304 stainless steel, aren't. Disposable hypodermic needles made from martensitic and ferritic stainless steel are easily detectable at the smallest size. Needles are conveniently made from 420 martensitic stainless steel or 430 ferritic stainless steel.

6 Claims, No Drawings

DETECTABLE STAINLESS STEEL NEEDLES FOR MEAT PACKING

This invention relates to a new use of stainless steel. Stainless steel hypodermic needles are used in raising livestock to be processed in meat packing plants. The needles break leaving metal in processed meat. Although metal detectors are employed in most meat packing plants, currently they don't detect stainless steel needles in meat.

BACKGROUND

Needles, which have broken off in livestock, are a problem in processed meat. Although disposable, in the field they are used repeatedly until they snap or break off in livestock (pigs and cattle). The needle has a stainless steel cannula fixed in a hub. The cannula breaks away from the hub or the cannula itself breaks, and remains unrecovered in the animal. Hubs are generally plastic (often polypropylene), aluminum, or chromium coated brass. Broken needles are more common in pork than beef because of the sheer volume of pigs processed each year. Needles will be present in processed meat from all livestock subject to injection. The current disposable needles used in the raising of livestock are usually made of 304 stainless steel, an austenitic alloy typically about 18 to 20% chromium and 8 to 12% nickel. It is not magnetic and needles made of it are not detectable by metal detectors currently used in meat plants, nor are other disposable hypodermic needles made of non-magnetic metals and alloys. One hundred million disposable hypodermic needles are used yearly. The current usage of disposable needles in the raising of livestock causes them to break. These undetectable needles end up in processed meat and pass through packing plants, which are sold to consumers, domestically and internationally. Many meat packing plants in North America use metal detectors in an attempt to detect and remove disposable hypodermic needles from processed meat. Despite this practice few, if any, disposable needles are detected and removed. For all practical purposes disposable hypodermic needles of austenitic 304 stainless steel and other non-magnetic metals and alloys are not detectable.

The problem is as at least as old as disposable hypodermic needles, and the meat packing industry is well aware of it. The problem has not been addressed by the needle manufacturers, who are also aware of the problem. The suggestion sometimes made that the stainless steel disposable needles should not be used in livestock raising, or at any rate not repeatedly used, is fanciful and not at all practical.

Although this suggestion is obviously ridiculous it is the sole suggestion to emerge from an in depth study at the Iowa State University, Ames (Hoff et. al., American Journal of Veterinary Research, 60, No.3, 292–298, 1999) which concluded that stainless steel needles and their hubs were sufficiently resilient to avoid breakage in single use. The contributory factor of breakage is that the animal moves when injected deforming the needle. The prime cause of breakage is that the deformed needle is straightened by hand and reused. The needle when straightened is much more likely to break off in the animal, and the chance increases with repeated straightening. While the manufacturers place product notices on needle packaging specifying "single use only", this is not followed in practice. The Iowa study also recommended "single use only."

There is increasing worry about disposable needles in the processed meat industry especially since complaints and presumably incidence are increasing. Export contracts are especially sensitive to the discovery of needles in meat. Two surveys were carried out in 1999 in Canada by the Canadian Cattlemen, a trade publication; one of veterinarians, one of processors, purveyors and retailers. The veterinarians (25% of whom had experienced broken needles) recommended use of proper animal restraints (50%, but difficult in practice), restricted reuse of the needle 5 to 20 times (41%), and discarding damaged needles (28%). Of the producers 41% had from 1 to 12 complaints about needles in the average year, 30% had metal detectors, and 31% used metal detectors (14% supplemented by visual inspection), about 14% passed all products through a metal detector, and another 14% passed some products through a metal detector. About 73% had high confidence in metal detection in trim (not whole muscle), 18% medium and 9% low. The surveys as summarized (Donkersgoed, Canadian Cattlemen, January 2000, p. 28) stated that the processors had little confidence in the ability of metal detectors to detect metal in large cuts of meat. As noted above, austenitic stainless steel is non-magnetic and one of the hardest metals to detect using a metal detector.

There are four groups involved, the needle manufacturers, veterinarians, producers, meat packers. Neither the packer nor the producer can rely on the other to detect needles in meat. In practice the packer is liable, because it is difficult if not impossible to identify the producer. Although some meat packing plants use metal detectors these are rarely successful in detecting needles.

There is therefore a need for detectable disposable needles. Current common needles come in several sizes especially 20 gauge×½ inch, 18 gauge×1 inch, 18 gauge×1½ inch, 16 gauge×1 inch, 16 gauge×1½ inch, 14 gauge×1 inch, 14 gauge×1½ inch, with larger needles used for larger animals and smaller needles for smaller animals. The primary need is to detect the smallest needles when broken off (20 gauge×½ inch), and preferably smaller broken portions of such needles.

PRIOR ART

Applicant is not aware of any prior art.

It is a principal object of the invention to provide hypodermic needles detectable in meat by metal detectors currently used in meat packing plants. It is a subsidiary object of the invention to provide hypodermic needles detectable in meat as broken portions by metal detectors currently used in meat packing plants.

DESCRIPTION OF THE INVENTION

The invention in its broadest aspect is directed to a magnetic stainless steel hypodermic needle detectable in meat by metal detectors. The magnetic stainless steel is preferably selected from the group of ferritic and martensitic stainless steels. The stainless steel may be ferritic, preferably 430 stainless steel, or it may be martensitic, preferably 420 stainless steel. The needle is preferably of length from ½ to 1½ inches long and gauge from 14 to 20. The needle may be of length ½ inch and gauge 20, of length 1 inch and gauge 18, of length 1½ inch and gauge 18, of length 1 inch and gauge 16, of length 1½ inch and gauge 16, of length 1 inch and gauge 14, of length 1½ inch and gauge 14.

In another aspect the invention is directed to the novel use of magnetic stainless steel in disposable hypodermic needles, detectable in meat by metal detectors. The magnetic stainless steel is preferably selected from the group consisting of ferritic and martensitic stainless steel. More preferably the stainless steel is martensitic stainless steel, conveniently 420 stainless steel. Also more preferably the stainless steel is ferritic stainless steel, conveniently 430 stainless steel.

In another aspect the invention is directed to the manufacture of disposable hypodermic needles detectable in meat by metal detectors from magnetic stainless steel. The magnetic stainless steel is preferably selected from the group consisting of ferritic and martensitic stainless steel. More preferably the stainless steel is martensitic stainless steel, conveniently 420 stainless steel. Also more preferably the stainless steel is ferritic stainless steel, conveniently 430 stainless steel. The preferred method of manufacture is cold drawing of tubular stock, which typically requires several iterations.

DESCRIPTION OF THE PREFERRED EMBODIMENT

The invention is illustrated but not restricted by reference to the preferred embodiments. It is well known that austenitic stainless steels are non-magnetic, and almost impossible to detect using metal detectors, which rely on distortion of an oscillating electromagnetic field. The reason is that non-magnetic stainless steel is a relatively poor conductor of electric current and has no magnetic properties and therefore not detectable. The stainless steel used in hypodermic needles is typically austenitic 304 stainless steel, and therefore not detectable.

Austenitic stainless steels are iron-chromium-nickel alloys with specified but variable carbon content, which are not hardenable by heat treatment, and are regarded as non-magnetic due to the nickel present. Martensitic stainless steels are iron-chromium alloys with no or little nickel content (less than 1%), hardenable by heat treatment, and regarded as magnetic. Ferritic stainless steels are iron-chromium alloys with no or little nickel content (less than 1%), are not hardenable by heat treatment, and regarded as magnetic. Ferritic stainless steels have a lower carbon content than martensitic stainless steels. These terms are well known to those skilled in the art. 304 stainless steel is the most common grade of austenitic stainless steel. 420 stainless steel, a martensitic stainless steel, has a higher carbon content than 410 stainless steel, the most common grade of martensitic stainless steel. 430 stainless steel is the most common grade of ferritic stainless steel.

Since stainless steel disposable needles are desirable, applicant decided to test other stainless steels to see if they could be detected. Applicant had no prior knowledge of whether magnetic stainless steel disposable needles would be detected by metal detectors in meat packing plants. A martensitic 420 stainless steel welding rod was reduced to approximately the size of a 20 gauge ½ inch needle for test purposes. It was then placed in meat and run through Loma and Safeline brand name metal detectors on meat production lines and easily detected, unexpectedly and to the surprise of applicant and to the amazement of everyone else. No one at the meat plants believed that the experimental rods of stainless steel that size could be detected. The experiment was repeated in 2 and 4 kilogram pork butts with bone, as bone is believed to affect metal detection, to convince both applicant and observer (packer). The 20 gauge ½ inch rod was detected on every trial. It was decided to manufacture a batch of needles for further testing. Unfortunately not only did 420 stainless prove impossible to obtain in the tubular form necessary for needle manufacture, but so did other martensitic stainless steels.

Ferritic stainless steel which is similar in composition, but not structure, was considered as a possible alternative. Ferritic 430 stainless steel was available in suitable tubular form. A small sample of 20 gauge 1 inch disposable cannulae (needles without hubs) were made up from this material and were similarly tested and detected. Again, applicant could not be certain before testing that the needles would be detectable, and nobody else had any inkling that they would be detectable. First 1 inch needles were tested in 2 and 4 kilogram pork butts with bone on meat production lines using Loma and Safeline brand name metal detectors and detected on every trial. Needles were then cut in half to simulate 20 gauge ½ inch needles, which were then tested in 2 and 4 kilogram pork butts with bone. Again, the needles were easily detected on every trial, to the amazement of observers.

Ferritic cannulae, 20 gauge 1 inch, were made up with chromium plated brass hubs as needles for injection testing. Generally, 430 stainless has lower tensile strength than 304 stainless so the question whether ferritic needles were as effective as austenitic needles arose. The ferritic needles were fitted onto a hypodermic syringe and tested by jabbing into a pork cadaver. Since the skin of pork cadavers toughens after death, the needles were tested about twenty-four hours after death. Forty-one punctures were made in the cadaver, using a single needle. When the 20 gauge needle deformed, it was finger straightened. The needle deformed with use, breaking at the forty first puncture. As far as applicant is aware this performance is comparable to existing 304 stainless needles. Since 430 stainless has less tensile strength than 304 stainless, the needle may deform and break with less use, but the practical difference is small.

There was no prior reason to believe that martensitic or ferritic stainless steel in the dimensions of disposable hypodermic needles would be detectable by metal detectors in meat production lines. There was thus no inkling or useful intention to combine martensitic or ferritic steel and the form of disposable hypodermic needles, which would be easily and routinely detected by metal detectors in meat processing lines. These detectors are set at high sensitivity to attempt (unsuccessfully) to detect the austenitic needles. Applicant was not faced with ignorance but active disbelief in the meat packing industry. Hearsay was not enough, demonstration was and is required to convince people.

The production batch of ferritic 430 stainless steel needles was made by cold drawing through a die from 2 inch diameter ⅜ inch wall thickness tubular stock. Some needles were fitted with brass hubs, some with plastic hubs. The hubs can be brass, aluminum, plastic (often polypropylene). Generally, several iterations of cold drawing are required. In the particular method used six were necessary.

By selecting magnetic stainless steel for disposable hypodermic needles applicant has solved a long standing problem in the meat industry.

As those skilled in the art would realize these preferred described details and materials and components can be subjected to substantial variation, modification, change, alteration, and substitution without affecting or modifying the function of the described embodiments.

Although embodiments of the invention have been described above, it is not limited thereto, and it will be apparent to persons skilled in the art that numerous modifications and variations form part of the present invention insofar as they do not depart from the spirit, nature and scope of the claimed and described invention.

I claim:

1. A system for detecting hypodermic cannulae or portions thereof embedded within meat, comprising;

a metal detector for detecting the presence of metal embedded in a meat sample; and a hypodermic cannula selected from magnetic stainless steel metals consisting of martensitic, ferritic, or mixtures thereof, said metals prepared by a plurality of cold drawings and in a size gauge of between 14 and 20.

2. The system as set forth in claim 1, wherein said stainless steel, consists of 420 stainless steel.

3. The system as set forth in claim 1, wherein said stainless steel, consists of 430 stainless steel.

4. A hypodermic needle cannula or portion thereof having high detectability in a meat sample, comprising:

a metal selected from magnetic stainless steel metals consisting of martensitic, ferritic, or mixtures thereof, said metals prepared, in a preparation step by a plurality of cold drawings and in a size gauge of between 14 and 20, whereby detectability of said needle cannula or portion thereof prepared according to said preparation step is greater than those prepared in the absence of said preparation step.

5. The hypodermic needle cannula as set forth in claim 4, wherein said stainless steel is selected from the group consisting of 430 and 420 stainless steel, or mixtures thereof.

6. A method of detecting hypodermic needle cannulae or portions thereof embedded within a meat sample, comprising:

providing a hypodermic needle cannula or portion thereof as set forth in claim 4;

providing a metal detector for detecting the presence of metal in a meat sample;

providing a meat sample for exposure to said metal detector;

exposing said sample to said detector; and detecting the presence of said needle cannula or portion thereof.

* * * * *